United States Patent [19]

Voeffray

[11] Patent Number: 4,936,958
[45] Date of Patent: Jun. 26, 1990

[54] PROCESS FOR PRODUCTION OF ENANTIOMERICALLY PURE 2,2,4-TRISUBSTITUTED 1,3-DIOXOLANES

[75] Inventor: Robert Voeffray, Basel, Switzerland

[73] Assignee: Lonza Ltd., Gampel/Valais, Switzerland

[21] Appl. No.: 298,019

[22] Filed: Jan. 18, 1989

[30] Foreign Application Priority Data

Jan. 26, 1988 [CH] Switzerland .......................... 253/88

[51] Int. Cl.$^5$ .............................................. C25B 3/00
[52] U.S. Cl. ....................................... 204/72; 204/78; 549/450; 549/451
[58] Field of Search ..................... 204/72, 78; 549/450, 549/451

[56] References Cited

PUBLICATIONS

M. M. Baizer et al., "Organic Electrochemistry an Introduction and Guide", 2nd edition Marcel Dekker Inc., New York, N.Y., pp. 510–511 (1983).
Hay, G. W.; et al., "Electrolysis of Low Molecular Weight Carbohydrates in Non-Aqueous Media. I. The Products of Electrolysis of Monosaccharides", Can. J. Chem. 47(3) 417–421 (1969).
Vértes, G.; "A New Method for the Electrochemical Oxidation of Alcohols"; Tetrahedron 28(1) pp. 37–42 (1972).

Primary Examiner—John F. Niebling
Assistant Examiner—Steven P. Marquis

Attorney, Agent, or Firm—Fisher, Christen & Sabol

[57] ABSTRACT

Enantiomer-free 2,2,4-trisubstituted 1,3-dioxolanes of the general formula:

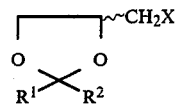

wherein $R^1$ and $R^2$ are either the same and are
(a) hydrogen or
(b) alkyl groups with 1 to 4 C atoms or
(c) aryl groups or
(d) arylalkyl groups or $R^1$ and $R^2$ together are a 1,4-butanediyl or 1,5-pentanediyl group, and X is either a hydroxy group or, with the assumption that $R^1$ and $R^2$ are not aryl groups, $NHR^3$ wherein $R^3$ is alkyl with 1 to 8 C atoms or aryl, are produced by electrolysis of a substated theronic acid or erythornic acid or a salt thereof into a substituted 1,3-dioxolane-4-carbaldehyde. The substituted 1,3-dioxolane-4-carbaldehyde is converted by reduction or reductive amination, without being ioslated, into the enantiomer-free 2,2,4-trisubstituted 1,3-dioxolane. A substantial advantage of the electrochemical process is that only carbon dioxide and hydrogen are produced which escape by themselves as gases from the electrolyte.

12 Claims, No Drawings

PROCESS FOR PRODUCTION OF ENANTIOMERICALLY PURE 2,2,4-TRISUBSTITUTED 1,3-DIOXOLANES

BACKGROUND OF THE INVENTION

1. Field of the Invention

The invention relates to a process for the production of enantiomerically pure 2,2,4 -trisubstituted 1,3-dioxolanes.

2. Background Art

Enantiomerically pure 2,2,4-trisubstituted 1,3-dioxolanes of the general formula:

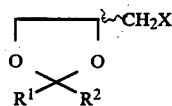
              I wherein X is OH or X is $NHR^3$, as derivatives of glycerin or 3-amino-1,2-propanediol, are extremely valuable chiral building blocks for stereospecific syntheses of natural products and of other optically active compounds, as, for example, pharmaceutical active ingredients. Some examples of these uses are the syntheses of (R)-4-amino-3-hydroxybutyric acid (GABOB) [J. Am. Chem. Soc. 102, 6304 (1980)], L carnitine (European Published Patent Application No. 0,060,595), acyclovir analogs [J. Med. Chem. 28, 926 (1985)] or beta-blockers (German OS No. 2810732).

Although some of these 1,3-dioxolanes, namely, the acetonides of glycerol ($R^1=R^2=CH_3$, X=OH), and some ethers and esters derived from them ($X=OCH_2C_6H_5$, O-tosyl) are already commercially available, the still very high price of these compounds prevents their use to a large extent. The numerous production processes known so far start from expensive feedstock (L-serine, L-arabinose) and/or expensive reagents used [lead(IV) acetate, $NaIO_4$, bismuth compounds, among others] and, therefore, do not allow production on an industrial scale and at attractive prices for reasons of costs.

A new process for the production of (S)-2,2-dimethyl-1,3-dioxolane-4-carbaldehyde (L-glyceraldehyde acetonide), (European Published Patent Application No. 0,143,973), from which the corresponding hydroxy compound can be obtained by reduction, for example, with sodium tetrahydridoborate, starts from 3,4-O-isopropylidene-L-threonic acid, which is degraded with hypochlorous acid or hypochlorite in an acid medium to the L-glyceraldehyde acetonide. Although 3,4-O-isopropylidene-L-threonic acid starting from L-ascorbic acid is easily available and the hypochlorite solution is a cheap chemical, such process still has some serious drawbacks:

The commercially available hypochlorite solutions vary in content and are not completely stable.

The free hypochlorous acid formed during the conducting of the process is still not very stable and partially decomposes, and, thus, more than the theoretically required amount is consumed.

An excess of hypochlorite still present after the course of the oxidation must be destroyed by the addition of a reduction agent. Thus, other extraneous materials are introduced into the reaction mixture.

The hypochlorite solution is very corrosive and requires a correspondingly resistant material for the apparatus used.

The hypochlorite solution used already contains large amounts of chloride, and further chloride is formed in the reaction. This total chloride amount must finally be disposed of; moreover, working up of the reaction mixture is possibly disturbed by the high salt concentration.

Performing the oxidation in an acid solution in the case of sensitive ketals and especially acetals can lead to hydrolysis of the ketal or acetal function and in these cases can make the process unusable.

BROAD DESCRIPTION OF THE INVENTION

The main object of the invention is to provide a process which does not exhibit such drawbacks and can be used for the production of a multiplicity of different substituted enantiomerically pure 2,2,4-trisubstituted 1,3-dioxolanes of general formula I set out herein. The main object of the invention is achieved by the process of the invention.

The invention involves a process for the production of enantiomerically pure 2,2,4-trisubstituted 1,3-dioxolanes of the general formula:

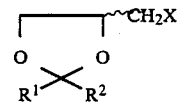
              I wherein $R^1$ and $R^2$ are either the same and are
(a) hydrogen or
(b) alkyl groups with 1 to 4 C atoms or
(c) aryl groups or
(d) arylalkyl groups or $R^1$ and $R^2$ together are a 1,4-butanediyl or 1,5-pentanediyl group, and X is either a hydroxy group or, with the assumption that $R^1$ and $R^2$ are not aryl groups, $NHR^3$ with $R^3$ being alkyl with 1 to 8 C atoms or aryl, characterized in that, depending on the desired configuration, a corresponding substituted threonic acid or erythronic acid of the general formula:

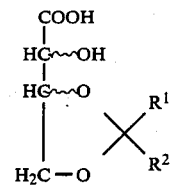
              II or a salt thereof is converted by electrolysis into the correspondingly substituted 1,3-dioxolane-4-carbaldehyde of the general formula:

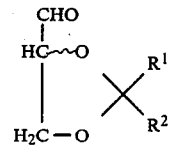
              III

The corresponding substituted 1,3-dioxolane-4-carbaldehyde without isolating it, is converted by reduction or reductive amination into the enantiomerically pure 2,2,4-trisubstituted 1,3-dioxolane according to formula I.

The oxidative decarboxylation of a threonic acid or erythronic acid of the general formula:

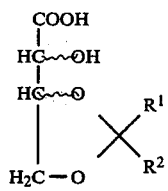

produces the corresponding glyceraldehyde derivative in good yield by electrolysis with the configuration on the beta-carbon atom being maintained. A substantial advantage of this electrochemical process is that, besides the desired product, only carbon dioxide and hydrogen are produced, which escape by themselves as gases from the electrolyte. Also, no excess of an oxidation agent, which would have to be eliminated after termination of the reaction, can occur.

Radicals $R^1$ and $R^2$ can be hydrogen or lower alkyl groups, preferably methyl or ethyl, especially methyl, or aryl groups, especially phenyl, or arylalkyl groups, especially benzyl. Further, $R^1$ and $R^2$ together can form a 1,4-butanediyl or especially 1,5-pentanediyl group, so that together with the carbon atom of the ketal function a five- or six-membered ring is produced.

Electrolysis suitably takes place in an aqueous medium, such as, a mixture of water with lower alcohols, acetonitrile, dimethylformamide, dimethyl sulfoxide, hexamethylphosphoric acid triamide or tetrahydrofuran, but preferably in water without additional solvent. A noble metal, such as, platinum, gold or iridium, or graphite can be used as the electrode material for the two electrodes but graphite is preferably used for the anode. An undivided cell, in which the solution is continuously circulated, is suitably used as the cell.

On a laboratory scale, performance of the electrolysis for example is also possible on platinum electrodes in a beaker, and the solution is stirred or thoroughly mixed with a rotating electrode. The current density is suitably 0.1 to 320 mA/cm$^2$, preferably 2 to 80 mA/cm$^2$; the electrolysis is preferably performed with a constant current. Normally 2 to 2.8 faraday/mol is consumed up to complete reaction. The temperature during electrolysis is suitably 5° to 90° C., preferably 10° to 70° C.

The pH of the solution during electrolysis is suitably between 4 and 10 and is kept in this range by the addition of acid, preferably sulfuric acid. The electrolysis is preferably performed at a pH of 6 to 7. The concentration of threonic acid or erythronic acid derivative during electrolysis is suitably between 0.5 and 25 percent, preferably 5 to 15 percent.

As the initial material preferably L-threonic acid or D-erythronic acid derivatives are used, which are produced from the corresponding L-ascorbic acid or D-isoascorbic acid (D-erythronic acid) derivatives of the general formula

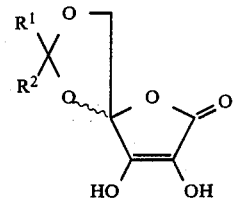

wherein $R^1$ and $R^2$ have the above-mentioned meanings, by oxidative cleavage, preferably with aqueous hydrogen peroxide in the presence of calcium carbonate (European Published Patent Application No. 0,111,326).

The L-threonic acid and D-erythronic acid derivatives in the last named production process accumulate as aqueous solutions of their calcium salts; in addition slightly soluble calcium oxalate is produced. In electrolysis of the calcium salts, a precipitation of calcium carbonate or calcium hydroxide on the electrodes occurs. Therefore, the calcium salts are suitably converted into an alkali salt or into the free acids by treatment with a cation exchanger. Then the free acid can be converted with a suitable base, preferably an alkali hydroxide or a tertiary amine, such as, triethylamine, into a salt suitable for electrolysis. The conversion of the calcium salt into the free acids can also take place by the calcium precipitating in the form of a slightly soluble salt. This can be achieved, for example, by the addition of sulfuric acid, which, with calcium, forms slightly soluble calcium sulfate.

But it has proven especially favorable to perform the oxidation of L-ascorbic acid or D-isoascorbic acid derivatives in the presence of an alkali carbonate, preferably sodium carbonate. Thus, the resultant L-threonic acid or the D-erythronic acid is obtained from the beginning in the form of alkali salt, while the calcium of the calcium carbonate, also added, binds the resultant oxalic acid only in the form of the slightly soluble calcium oxalate. The alkali carbonate is suitably added in an amount of 0.5 to 2 mol (relative to 1 mol of L-ascorbic acid or D-isoascorbic acid derivative).

The glyceraldehyde derivative obtained by electrolysis can be isolated by the usual extraction process and purified by distillation in a vacuum. But since glyceraldehyde derivatives are only slightly stable, it is advisable not to isolate them but to react them further directly in the reaction mixture. In the process according to the invention, this reaction takes place by reduction of the aldehyde function to the hydroxymethyl group or by reduction in the presence of a primary amine, preferably a lower alkyl amine, such as, isopropylamine, with formation of a secondary amino group.

The reduction is preferably performed by catalytic hydrogenation, especially on Raney nickel or palladium catalysts; reduction to the hydroxymethyl group can also take place especially with sodium tetrahydridoborate. It is also possible to convert the glyceraldehyde derivative into a more stable compound by another reaction, for example, the formation of a Schiff base with an amine (European Published Patent Application Nos. 0,120,289 and 0,143,973).

EXAMPLE 1

5,6-O-isopropylidene-L-ascorbic acid 10.0 g (55 mmol) of L-ascorbic acid was added to a solution of 1 ml of acetyl chloride in 40 ml of acetone.

The heterogeneous mixture was stirred for 3 hours at room temperature and then 8 hours at 0° to 5° C. The product was filtered off, washed twice with 5 ml of cold acetone each time and dried. The yield was 9.65 g (81.1 percent). The product had a melting point of 223° to 226° C. The product had the following properties:

$[\alpha]_D^{20} = +10.5°$ (c=5, methanol)

H$^1$-NMR: (CD$_3$OD, 300 MHz) δ: 1.34 (s,3H); 1.37 (s, 3H); 4.04 (dd, J=8.5/6.5 Hz, 1H, H-C(6)); 4.17 (dd, J=8,5/7 Hz, 1H, H-C(6)); 4.33 (ddd, J=7/6.5/3 Hz, 1H, H-C(5)); 4.67 (d, J=3 Hz, 1H, H-C(4)).

EXAMPLE 2

5,6-O-cyclohexylidene-D-isoascorbic acid

In a 200-ml three-neck flask, 4.45 g (45.2 mmol) of cyclohexanone, 7.05 g (47.5 mmol) of triethyl orthoformate, 0.04 g of p-toluenesulfonic acid (monohydrate), 4.15 g (90 mmol) ethanol and 95 ml of ethyl acetate were heated to 100° C. and kept at this temperature for 1 hour (reflux). Thus, 1,1-diethoxycyclohexane was formed. Then 4.0 g (22.7 mmol) of D-isoascorbic acid was added and the first heterogeneous mixture was refluxed for 5 hours, and a clear solution was formed. Then 2 g of aluminum oxide was added, the suspension was stirred for 1 more hour at room temperature and filtered over Celite ®, which was rewashed three times with ethyl acetate. The filtrate was concentrated by evaporation at 35° C./30 mbars to 20.5 g, and a viscous pulp was formed. The product was completely precipitated by addition of 20 ml of hexane, filtered off and dried. The yield was 5.05 g (86.8 percent). The product had a melting point: 177° to 178.5° C. The product had the following properties:

$^1$H-NMR: (Acetone-d$_6$, 300 MHz) δ: 1.30–1.50 (m, 2H); 1.50–1.70 (m, 8H); 2.97 (m, 2H, OH); 3.77 (dd, J=8.5/6 Hz, 1H, H-C(6)); 4.01 (dd, J=8.5/7 Hz, 1H, H-C(6)); 4.42 (ddd, J=7/6/4 Hz, 1H, H-C(5)); 4.84 (d, J=4 Hz, 1H, H-C(4)).

EXAMPLES 3 to 8

The following ketals were produced analogously to Example 2.

EXAMPLE 3

5,6-O-cyclopentylidene-D-isoascorbic acid

The yield was 61 percent. The product has the following properties:

$^1$H-NMR: (CD$_3$OD, 300 MHz) δ: 1.60–2.05 (m, 8H); 3.73 (dd, J=8.5/6 Hz, 1H, H-C(6)); 3.91 (dd, J=8.5/7.5 Hz, 1H, H-C(6)); 4.36 (ddd, J=7.5/6/3 Hz, 1H, H-C(5)); 4.82 (d, J=Hz, 1H, H-C(4)).

EXAMPLE 4

5,6-O-(1-ethylpropylidene)-D-isoascorbic acid

The yield was 57 percent. The product had the following properties:

$^1$H-NMR: (CD$_3$OD, 300 MHz) δ: 0.89 (t, 3H); 0.91 (t, 3H); 1.61 (q, 2H); 1.69 (q, 2H); 3.75 (t, J=7 Hz, 1H, H-C(6)); 3.99 (t, J=7Hz, 1H, H-C(6)); 4.45 (td, J=7/3 Hz, 1H, H-C(5)); 4.88 (d, J=3 Hz, 1H, H-C(4)).

EXAMPLE 5

5,6-O-isopropylidene-D-isoascorbic acid

The yield was 41 percent. The product had the following properties:

$^1$H-NMR: (CD$_3$OD, 300 MHz) δ: 1.35 (s, 3H); 1.42 (s, 3H); 3.78 (dd, J=8.5/6.5 Hz, 1H, H-C(6)); 4.00 (dd, J=8.5/7 Hz, 1H, H-C(6)); 4.44 (ddd, J=7/6.5/4 Hz, 1H, H-C(5)); 4.83 (d, J=4 Hz, 1H, H-C(4)).

EXAMPLE 6

5,6-O-cyclohexylidene-L-ascorbic acid

The yield was 67 percent. The product had the following properties:

$^1$H-NMR: (CD$_3$OD, 300 MHz) δ: 1.30–1.48 (m, 2H); 1.48–1.65 (m, 8H); 4.02 (dd, J=8/6.5 Hz, 1H, H-C(6)); 4.16 (dd, J=8/7 Hz, 1H, H-C(6)); 4.31 (ddd, J=7/6.5/3 Hz, 1H, H-C(5)); 4.65 (d, J=3 Hz, 1H, H-C(4)).

EXAMPLE 7

5,6-O-cyclohexylidene-L-ascorbic acid

The yield was 73 percent. The product had the following properties:

$^1$H-NMR: (CD$_3$OD, 300 MHz) δ: 1.55–1.85 (m, 8H); 4.00 (dd, J=8.5/6 Hz, 1H, H-C(6)); 4.10 (dd, J=8.5/7 Hz, 1H, H-C(6)); 4.26 (ddd, J=7/6.5/3 Hz, 1H, H-C(5)); 4.66 (d, J=3 Hz, 1H, H-C(4)).

EXAMPLE 8

5,6-O-(1-ethylpropylidene)-L-ascorbic acid

The product has the following properties:

$^1$H-NMR: (CD$_3$OD, 300 MHz) δ: 0.80–0.95 (m, 6H); 1.55–1.70 (m, 4H); 4.00 (t, J=7 Hz, 1H, H-C(6)); 4.18 (t, J=7 Hz, 1H, H-C(6)); 4.32 (td, J=7/3 Hz, 1H, H-C(5)); 4.69 (d, J=3 Hz, 1H, H-C(4)).

EXAMPLE 9

Calcium-3, 4-O-isopropylidene-L-threonate

In a 200-ml three-neck flask, 8.0 g (80 mmol) of calcium carbonate was suspended at room temperature in 100 ml of water and 8.65 g (40 mmol) of 5,6-O-isopropylidene-L-ascorbic acid was added within 30 minutes by portions. After cooling to 5° C., 18.15 g of hydrogen peroxide (30 percent solution in water, 160 mmol) was added within 2 hours, and the temperature was kept below 20° C. The heterogeneous mixture was stirred for 2 more hours at room temperature and for 30 minutes at 40° C. and, after addition of 2 g of activated carbon, was heated in 1 hour to 85° C. The resulting calcium oxalate and the activated carbon were filtered over Celite ® and the filtrate was concentrated by evaporation to 50 g. The product was precipitated by addition of 60 ml of acetone. The yield was 6.2 g (77.4 percent) of calcium-3,4-O-isopropylidene-L-threonate ¼ H$_2$O. The melting point of the product was greater than 250° C. The product had the following property:

$[\alpha]_D^{20} = +21.5°$ (c=1, H$_2$O)

EXAMPLE 10

Calcium-3,4-O-cyclohexylidene-D-erythronate 18.15 g of hydrogen peroxide (30 percent solution in water, 1.60 mmol) was added to a suspension of 8.0 g (80 mmol) of calcium carbonate and 10.2 g (40 mmol) of 5,6-O-cyclohexylidene-D-isoascorbic acid in 150 ml of water within 2 hours, and the temperature was kept below 20° C. The heterogeneous mixture was stirred for 2 more hours at room temperature and for 45 minutes at 40° C. and, after addition of 2 g of activated carbon, was heated for 1 hour to 90° C. The resulting calcium oxalate and the activated carbon were filtered over Celite ® and the filtrate was concentrated by evaporation to 52.5 g. The product was precipitated by instillation of 60 ml of ethanol. The yield was 8.4 g (86 percent) of calcium-3,4-O-cyclohexylidene-D-erythronate ½ H₂O. The melting point of the product was greater than 250° C. The product had the following property:

$[\alpha]_D^{20} = +18.8°$ (c=1, ethanol)

EXAMPLE 11

(R)-2,2-dimethyl-1,3-dioxolane-4-methanol from calcium-3,4-o-isopropylidene-L-threonate (electrolysis in the presence of triethylamine)

10.0 g of sulfuric acid (50 percent, 50 mmol) was instilled in a solution of 23.8 g of calcium-3,4-O-isopropylidene-L-threonate (82 percent, 100 mmol) in 220 ml of water. Then the pH was 1.95 and the heterogeneous mixture was stirred for 10 more minutes at 0° to 5° C. The precipitated calcium sulfate dihydrate was filtered off and washed twice with 10 ml of water each time. The filtrate was mixed with 6.2 g (60 mmol) of triethylamine and electrolyzed in an undivided electrolysis cell of 250 ml in volume on graphite electrodes at 15° to 20° C. and a constant current of 1.0 A for 6.5 hours. The pH, which at the end of electrolysis was 8.0 to 8.5, was brought to 7 to 8 by addition of 15 g of disodium hydrogenphosphate (dodecahydrate). The mixture was cooled to 0° C., mixed by portions within 1.5 hours with 7.8 g (200 mmol) of sodium tetrahydridoborate, stirred for 7 hours more at 20° C. and then filtered. The filtrate was extracted six times with 200 ml of ether, the organic phases were dried over sodium sulfate and concentrated by evaporation. The residue was distilled at 24 mbars over potassium hydroxide. The yield was 6.95 g (52 percent). The product had a boiling point of 85° to 87° C./24 mbar. The following data concerns the product:

$[\alpha]_D^{20} = -15.3°$ (neat)
Content 98.8 percent (GC).

EXAMPLE 12

(R)-2,2-dimethyl-1, 3-dioxolane-4-methanol from 5,6-O-isopropylidene-L-ascorbic acid (oxidation and electrolysis in the presence of sodium carbonate).

A mixture of 10.0 g (100 mmol) of calcium carbonate and 15.9 g (150 mmol) sodium carbonate was added by portions to a solution of 21.6 g of 5,6-O-isopropylidene-L-ascorbic acid (95 percent, 95 mmol) in 250 ml of water within 15 minutes. The heterogeneous mixture was stirred for 1 more hour at room temperature and then cooled to 10° C. Then 44.5 g of hydrogen peroxide (30 percent solution in water, 400 mmol) was instilled within 1 hour, and the temperature was kept below 20° C. The mixture was stirred one more hour at room temperature and 1 hour at 40° C., then mixed by portions with 4 g of activated carbon and stirred for 1 hour more at 75° C. After cooling to 50° C., the mixture was filtered over Celite ®, the filtrate was cooled in a thermostated beaker to 15° C. and adjusted to pH 6.5 by addition of sulfuric acid and kept at this pH during electrolysis. The electrolysis took place in tube (d=3 cm) with 2 cathodes and 2 anodes made of graphite (d=0.5 cm, l=24 cm) at a current of 2.2 A, and the solution was continuously circulated by a pump. A total of 2.5 faraday/mol was consumed. After electrolysis the pH was adjusted to 7 to 8 by addition of 15 g of disodium hydrogenphosphate (dodecahydrate), the mixture was cooled to 0° C. and within 1.5 hours was mixed by portions with 7.8 g (200 mmol) of sodium tetrahydridoborate. Then the heterogeneous mixture was stirred for 4 more hours at 20° C. and then filtered. The filtrate was extracted six times with 100 ml of ethyl acetate each time and the raw product obtained by concentrated by evaporation was distilled in a vacuum. The yield was 7.5 g (56.4 percent). The following data concerns the product:

$[\alpha]_D^{20} = -15.12°$ (neat)
Content: 99.3 percent (GC).

EXAMPLE 13

(R)-2,2-dimethyl-1,3-dioxolane-4-methanol from 5,6-O-isopropylidene-L-ascorbic acid (electrolysis on Pt electrodes)

As described in Example 12, 9.1 g of 5,6-O-isopropylidene-L-ascorbic acid (95 percent, 40 mmol) was oxidized with hydrogen peroxide in the presence of calcium carbonate and sodium carbonate. Electrolysis of the resulting solution of sodium-3,4-O-isopropylidene-L-threonate was performed at 15° C. in a thermostated beaker. A rotating (2000 l/minute) platinum disk (A=3 cm²) was used as anode, which at the same time performed the thorough mixing of the solution. A platinum wire gauze (A=6.2 cm²) was used as cathode. A constant current of 0.6 A up to an amount of electricity of 2.5 faraday/mol was conducted through the solution. The other steps took place as described in Example 12. The yield was 2.0 g (37.4 percent). The product had a boiling point of 75° to 77° C./12 torr. The following data concerns the product:

$[\alpha]_D^{20} = -15.3°$ (neat)
Content: 99.1 percent (GC)

EXAMPLE 14

(S)-1,2-O-cyclohexylideneglycerol from calcium-3,4-O-cyclohexylidene-D-erythronate A solution of 24.8 g of calcium-3,4-O-cyclohexylidene-D-erythronate (95 percent, 100 mmol; produced according to example 10) in 160 ml of methanol was added to a column of 500 g of Dowex ® 50W (protonated form) and eluted with 1.5 l of methanol. The elute was concentrated by evaporation to 120 g and mixed with a solution of 6.2 g (60 mmol) of triethylamine in 100 ml of water. The other steps were performed as described in Example 11. The yield was 6.0 g (35 percent). The product had a boiling point of 87° to 89° C./1 torr, 137° C./17 torrs. The following data concerns the product:

$[\alpha]_D^{20} = +7.3°$ (c=2, methanol)
¹H-NMR: (CDCl₃, 300 MHz) δ: 1.30–1.50 (m, 2H); 1.50–1.70 (m, 8H); 3.04 (t, J=6 Hz, 1H, OH); 3.59 (ddd, J=11.5/6/5.5 Hz, 1H, H-C(3)); 3.70 (ddd, J=10/6/4.5 Hz, 1H, H-C(3)); 3.77 (dd, J=8/6.5 Hz, 1H, H-C(1)); 4.03 (dd, J=8/6.5 Hz, 1H, H-C(1)); 4.23 (tdd, J=6.5/5.5/4 Hz, 1H, H-C(2)).
Content: 96.6 percent (CG)

EXAMPLE 15

(S)-1,2-O-cyclohexylideneglycerol from 5,6-O-cyclohexylidene-D-isoascorbic acid

A solution of 25.7 g of 5,6-O-cyclohexylidene-D-isoascorbic acid (95 percent; 95 mmol; produced according to Example 2) in 250 ml of water was oxidized in the presence of calcium carbonate and sodium carbonate with hydrogen peroxide as described in Example 12 and then electrolyzed. The yield was 5.7 g (34.7 percent). The following data concerns the product:

$[\alpha]_D^{20} = +7.4°$ (c=5, methanol)

Content: 98.7 percent (GC)

EXAMPLE 16

(S)-1,2-O-cyclocpentylideneglycerol from 5,6-O-cyclopentylidene-D-isoascorbic acid.

A mixture of 4.0 g (40 mmol) of calcium carbonate and 6.4 g (60 mmol) of sodium carbonate was added by portions within 10 minutes to a solution of 10.2 g of 5,6-O-cyclopentylidene-D-isoascorbic acid (95 percent, 40 mmol; produced according to Example 3) in 150 ml of water. The heterogeneous mixture was stirred for 1 more hour at room temperature and then cooled to 10° C. Then within 1 hour 18.15 g of hydrogen peroxide (30 percent solution in water, 160 mmol) was instilled so that the temperature remained below 20° C. The mixture was stirred for 1 hour more at room temperature and for 1 hour at 40° C. and then mixed within 30 minutes with 2 g of activate carbon. Then it was stirred for 1 hour more at 85° C. and, after cooling to 50° C., was filtered over Celite ®. The filtrate was cooled to 15° C. in a thermostated beaker and brought to a pH of 6.5 by addition of sulfuric acid and was kept at this pH during electrolysis. Electrolysis was performed in a tube (d=3 cm) on 2 cathodes and 2 anodes of graphite (d=0.5 cm, l=7 cm) with 1.6 A and a total of 2.5 faraday/mol was consumed, and the solution was continuously circulated by a pump. Then the pH was brought to 7 to 8 by addition of 6.0 g of disodium hydrogenphosphate (dodecahydrate) and the mixture was cooled to 0° C. 3.1 g (80 mmol) of sodium tetrahydridoborate was added by portions within 1 hour. The heterogeneous mixture was stirred for 4 more hours at 25° C. and then filtered. The filtrate was extracted five times with 50 ml of ethyl acetate each time and the extract was distilled in a vacuum after the solvent was distilled off. The yield was 2.7 g (42.3 percent). The product had a boiling point of 86° to 87° C./1 torr. The following data concerns the product:

$[\alpha]_D^{20} = +8.9°$ (c=5, methanol)

$^1$H-NMR: (CDCl$_3$, 300 MHz) δ: 1.60–2.00 (m, 8H); 3.55–3.70 (m, 3H); 3.78 (dd, J=8/7 Hz, 1H, H-C(1)); 4.02 (dd, J=8/6 Hz, 1H, H-C(1)); 4.20 (dddd, J=7/6/5/4.5 Hz, 1H, H-C(2)).

Content: 99.1 percent (GC)

EXAMPLE 17

(S)-2,2-diethyl-1,3-dioxolane-4-methanol from 5,6-O-(1-ethylpropylidene)-D-isoascorbic acid 18.5 g of hydrogen peroxide (30 percent solution in water, 160 mmol) was instilled within 2 hours in a suspension of 4.0 g (40 mmol) of calcium carbonate, 6.4 g (60 mmol) of sodium carbonate and 10.3 g of 5,6-O-(1-ethylpropylidene)-Disoascorbic acid (95 percent, 40 mmol; produced according to Example 4) in 150 ml of water, and the temperature by cooling was kept below 20° C. The heterogeneous mixture was stirred for 2 more hours at room temperature and 45 minutes at 40° C. and, after addition of 2 g of activated carbon, was heated in for 1 hour to 85° C. The calcium oxalate formed and the activated carbon were filtered off, the filtrate was put into a beaker thermostated at 40° C. and adjusted to pH 6.5 with sulfuric acid and kept at this pH during electrolysis. Electrolysis was performed in a tube (d=3 cm) on 2 cathodes and 2 anodes of graphite (d=0.5 cm, l=7 cm) at 1.2 A and a total of 2.5 faraday/mol, and the solution was continuously circulated by a pump. After termination of electrolysis, 6 g of disodium hydrogenphosphate (dodecahydrate) was added to bring the pH to 7 to 8. The mixture was cooled to 0° C. and mixed with 3.1 g (80 mmol) of sodium tetrahydridoborate by portions within 2 hours. After this addition, it was stirred for 4 more hours at 25° C. and then filtered. The filtrate was extracted five times with 50 ml of ethyl acetate each time and the raw product, obtained from the extract, after the solvent was distilled off, was distilled in a vacuum. The yield was 2.45 g (38.3 percent). The product had a boiling point of 58° to 61° C./0.2 torr. The following data concerns the product:

$[\alpha]_D^{20} = +13.6°$ (c=5, methanol)

$^1$H-NMR: (CDCl$_3$, 300 MHz) δ: 0.93 (t, 3H); 0.95 (t, 3H); 1.65 (q, 2H); 1.69 (q, 2H); 2.17 (s, 1H, OH); 3.61 (dd, J=11/5 Hz, 1H, H-C(3)); 3.74 (m, 1H, H-C(3)); 3.75 (dd, J=8/7 Hz, 1H, H-C(1)); 4.03 (dd, J=8/7 Hz, 1H, H-C(1)); 4.23 (m, 1H, H-C(2)).

Content: 98.7 percent (GC)

EXAMPLE 18

(S)-2,2-dimethyl-1,3-dioxolane-4-methanol from 5,6-O-isopropylidene-D-isoascorbic acid.

Analogously to Example 12, the (S)-2,2-dimethyl-1,3-dioxolane-4-methanol was produced form 5,6-O-isopropylidene-D-isoascorbic acid by oxidation with hydrogen peroxide in the presence of calcium carbonate and sodium carbonate and then electrolysis. The yield was 58.2 percent. The product had a boiling point of 75° to 78° C./12 torr. The following data concerns the product:

$[\alpha]_D^{20} = +11.5°$ (c=5, methanol)
$[\alpha]_D^{20} = +15.1°$ (neat)

$^1$H-NMR: (CDCl$_3$, 300 MHz) δ: 1.39 (s, 3H); 1.46 (s, 3H); 2.32 (s, 1H, OH); 3.61 (dd, J=11.5/5 Hz, 1H, H-C(3)); 3.74 (dd, J=11.5/4 Hz, 1H, H-C(3)); 3.80 (dd, J=8/6.5 Hz, 1H, H-C(1)); 4.04 (dd, J=8/6.5 Hz, 1H, H-C(1)); 4.25 (tdd, J=6.5/5/4 Hz, 1H, H-C(2)).

EXAMPLE 19

(R)-4-isopropylaminomethyl-2,2-dimethyl-1,3-dioxolane from 5,6-O-isopropylidene-L-ascorbic acid A solution of (S)-2,2-dimethyl-1,3-dioxolane-4-carbaldehyde (amount and performance as in Example 12, but without reduction with sodium tetrahydridoborate) produced according to Example 12 was instilled within 3 hours under a hydrogen atmosphere in a mixture of 20 ml isopropylamine, 2.0 g of palladium/activated carbon (10 percent Pd) and 200 ml of methanol. The mixture hydrogenated in a shaking apparatus at 3 bars of hydrogen pressure and room temperature to the termination of the hydrogen absorption. Then the catalyst was filtered off and the filtrate was concentrated to 100 ml by evaporation. After addition of 10 g of sodium carbonate the mixture was extracted five times with 50 ml of dichloromethane each time, the dichloromethane phases were dried on sodium sulfate and the solvent was distilled off. The oily residue was then distilled in a vacuum. The yield was 6.8 g (41.4 percent, relative to 5,6-O-isopropylidene-L-ascorbic acid). The boiling point was 43° to 45° C./0.1 torr. The product had the following property:

$[\alpha]_D^{20} = +7.3°$ (c=2, methanol).

What is claimed is:

1. Process for production of enantiomer-free 2,2,4trisubstituted 1,3-dioxolanes of the general formula:

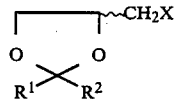

wherein R$^1$ and R$^2$ are either the same and are
(a) hydrogen or
(b) alkyl groups with 1 to 4 C atoms or
(c) aryl groups or
(d) arylalkyl groups or R$^1$ and R$^2$ together are a 1,4-butanediyl or 1,5-pentanediyl group, and X is either a hydroxy group or, with the assumption that R$^1$ and R$^2$ are not aryl groups, NHR$^3$ wherein R$^3$ is alkyl with 1 to 8 C atoms or aryl, characterized in that (a), depending on the desired configuration, a corresponding substituted threonic acid or erythronic acid of the general formula:

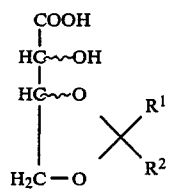

or a salt thereof is converted by electrolysis into the correspondingly substituted 1,3-dioxolane-4-carbaldehyde of the general formula:

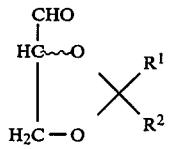

and (b), the corresponding substituted I,3-dioxolane-4-carbaldehyde, without being isolated is converted by reduction or reductive amination into the enantiomer-free 2,2,4-trisubstituted 1,3-dioxolane according to formula I.

2. Process according to claim 1 wherein electrolysis is performed in an aqueous solution at pH 4 to 10.

3. Process according to claim 2 wherein the electrolysis is performed in the presence of a tertiary amine.

4. Process according to claim 2 wherein the threonic acid or erythronic acid is used in the form of an alkali or alkaline-earth salt.

5. Process according to claim 4, wherein the threonic acid or erythronic acid is produced by the oxidative degradation of a correspondingly substituted ascorbic acid or isoascorbic acid of the general formula:

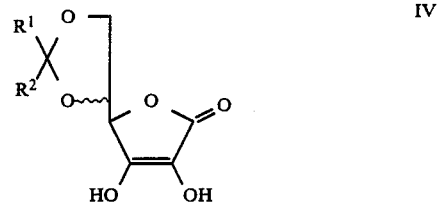

with aqueous hydrogen peroxide in the presence of calcium carbonate.

6. Process according to claim 5 wherein the oxidation of the ascorbic acid or isoascorbic acid takes place in the presence of an alkali carbonate.

7. Process according to claim 1 wherein the electrolysis is performed in the presence of a tertiary amine.

8. Process according to claim 1, wherein the threonic acid or erythronic acid is used in the form of an alkali or alkaline-earth salt.

9. Process according to claim 1 wherein the threonic acid or erythronic acid is produced by the oxidative degradation of a correspondingly substituted ascorbic acid or isoascorbic acid of the general formula:

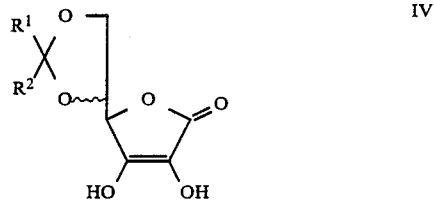

with aqueous hydrogen peroxide in the presence of calcium carbonate.

10. Process according to claim 9 wherein the oxidation of the ascorbic acid or isoascorbic acid takes place in the presence of an alkali carbonate.

11. Process according to claim 1 wherein, in formula I, X is a hydroxy group and, in step (b), the conversion is achieved by reduction.

12. Process according to claim 1 wherein, in formula I, X is NHR$^3$ and, in step (b), the conversion is achieved by reductive amination.

* * * * *

UNITED STATES PATENT AND TRADEMARK OFFICE
CERTIFICATE OF CORRECTION

PATENT NO. : 4,936,958
DATED : June 26, 1990
INVENTOR(S) : Robert Voeffray

It is certified that error appears in the above-identified patent and that said Letters Patent is hereby corrected as shown below:

On the title page:

[57]   ABSTRACT

Line 13, cancel "substated" and insert --substituted--.

Line 14, cancel "erythornic" and insert --erythronic--.

Signed and Sealed this

Twentieth Day of August, 1991

Attest:

HARRY F. MANBECK, JR.

Attesting Officer

Commissioner of Patents and Trademarks